United States Patent [19]

Golias

[11] Patent Number: 4,720,788
[45] Date of Patent: Jan. 19, 1988

[54] DIAGNOSTIC DENSITOMETER

[75] Inventor: Tipton L. Golias, Beaumont, Tex.

[73] Assignee: Helena Laboratories Corporation, Beaumont, Tex.

[21] Appl. No.: 49,002

[22] Filed: May 7, 1987

Related U.S. Application Data

[63] Continuation of Ser. No. 622,610, Jun. 20, 1984, abandoned.

[51] Int. Cl.[4] .................. G06F 15/42; G01N 33/16
[52] U.S. Cl. .................... 364/416; 204/180.1; 204/299 R
[58] Field of Search ............... 364/414, 416, 415; 436/63, 169; 204/299, 180

[56] References Cited

U.S. PATENT DOCUMENTS

| | | | |
|---|---|---|---|
| Re. 28,803 | 5/1976 | Durkos et al. | 235/151.35 |
| 3,706,877 | 12/1972 | Clifford, Jr. et al. | 235/151.35 |
| 3,916,176 | 10/1975 | Alien et al. | 235/151.35 |
| 3,977,394 | 8/1976 | Jones et al. | 128/2.08 |
| 4,045,655 | 8/1977 | Suzuki et al. | 235/92 |
| 4,097,845 | 6/1978 | Bacus | 340/146.3 |
| 4,122,518 | 10/1978 | Castleman et al. | 364/415 |
| 4,186,748 | 2/1980 | Schlager | 128/736 |
| 4,197,854 | 4/1980 | Kasa | 128/630 |
| 4,199,748 | 4/1980 | Bacus | 340/146.3 |
| 4,210,419 | 7/1980 | Castleman | 364/415 |
| 4,216,462 | 8/1980 | McGrath et al. | 364/415 |
| 4,218,737 | 8/1980 | Buscher et al. | 364/493 |
| 4,232,970 | 11/1980 | Sawamura et al. | 356/432 |
| 4,242,730 | 12/1980 | Golias et al. | 364/416 |
| 4,295,949 | 10/1981 | Fujiwara | 204/182.8 |
| 4,312,728 | 1/1982 | Kamachi | 204/229 R |
| 4,344,142 | 8/1982 | Diehr, II et al. | 364/473 |
| 4,420,384 | 12/1983 | Fujiwara | 364/416 |

FOREIGN PATENT DOCUMENTS 28834 3/1977 Japan.

OTHER PUBLICATIONS

Medical Laboratory Observer, Jul. 1981, Published by Medical Economics Company, Oradell, N.J. 07649, Entitled "Computerized Diagnosis in the Lab".
"Monoclonal Gammopathy", National Clinical Chemistry Mtg., (Anaheim, Calif., Aug. 1982), pp. 41–45.
L. Killingsworth et al, "Protein Analysis . . . ", *Diagnostic Medicine*, pp. 47–58, (Jan./Feb. 1980).
A. Pierce, et al, "New Approaches to Protein Analysis", American Society Clinical Pathologists National Meeting, 1981, pp. 1–25.
B. Janik, *High Resolution Electrophoresis and Immunofixation of Serum Proteins on Cellulosic Media;* (Gelman Sciences, 3rd Revised Ed., Apr. 1982), pp. 66–82.

*Primary Examiner*—Jerry Smith
*Assistant Examiner*—Gail O. Hayes
*Attorney, Agent, or Firm*—Cullen, Sloman, Cantor, Grauer, Scott & Rutherford

[57] ABSTRACT

A diagnostic densitometer for scanning a blood sample to automatically determine serum protein fractions and to provide an analog trace indicative of the serum protein fractions. The analog trace is edited by the operator of the densitometer and additional data is provided by the operator of the densitometer. Thereafter, the densitometer evaluates the edited analog trace and the additional data and compares them to an internal data base to interpret the same and provides a preliminary medical diagnosis.

20 Claims, 5 Drawing Figures

DIAGNOSTIC DENSITOMETER

This application is a continuation of application Ser. No. 622,610 filed on June 20, 1984, now abandoned.

BACKGROUND OF THE INVENTION

This invention relates generally to densitometers and, more particularly, to an improved diagnostic densitometer which provides both analog and digital outputs and which interprets the outputs to provide a preliminary medical diagnosis.

Densitometers are well-known as devices which scan a sample and provide an output signal or graphical display indicative of the optical density, transmittance, absorption or the like of the scanned sample.

One well-known use of the densitometer is to scan a sample of blood which has been prepared by the electrophoresis process. Electrophoresis of blood samples isolates various proteins in the blood, known as albumin, alpha-1 globulin, alpha-2 globulin, beta-globulin and gamma-globulin. The electrophoresis technique separates these proteins from each other and then the sample may be processed or scanned in a densitometer. Each of the proteins exhibits a different light absorption characteristic or pattern and the light absorption patterns are graphically displayed by the densitometer to indicate the presence and quantity of each of these proteins.

The graphical display may include a first analog signal or curve which exhibits a series of peaks and valleys. In the analysis of blood, the area under the optical density curve and bounded by the two adjacent valleys separated by one peak, is representative of the quantity of each protein in the sample and is referred to a sample fraction. The important data is the relative percentage of each protein and the selection of these fraction boundaries, i.e., the precise locations of these valleys is somewhat arbitrary and results in inaccurate analysis of the blood sample. The problem is not unique to evaluation of blood samples, but is common to optical and magnetic density valuations and, in fact, to all evaluations of analog data.

It is known, according to the prior art, to provide a microprocessor-controlled densitometer to scan an electrophoretically prepared sample and provide both an analog signal or curve of the optical density and digital (i.e., numerical) data representative of the quantity of each protein and/or the relative amount of each protein in the sample. Such a densitometer is described, for example, in U.S. Pat. No. 4,242,730 of Golias et al issued Dec. 30, 1980.

Heretofore, once the analog and digital data were provided by the densitometer a physician would interpret the data and provide a medical diagnosis. The diagnosis, of course, would be based upon the physician's own prior experience, education and knowledge, and would also be based upon other medical information about the patient.

Prior to the present invention it was also known that computers could be provided with a data base and could make decisions based upon a comparison of self-generated or externally provided data with the data base.

For example and not by way of limitation, Japanese Pat. No. 28834 of Apr. 3, 1977 discloses a device which attempts to identify a disease based upon data contained in a data base plus the input of clinical data with respect to an individual patient.

Jones et al U.S. Pat. No. 3,977,394 of 1976 relates to a computerized pulmonary analyzer and, more specifically to a programmable digital computer which receives a signal representative of the volume of air expelled by a patient upon exhaling, and with the computer comparing the test results with internal standardized values and providing an output signal comparing the test data to the standardized values.

U.S. Pat. No. 4,199,748 to Bacus relates to a method and apparatus which assists in diagnosis for anemic blood and the like by comparing microscopic slides to a pattern recognition program.

U.S. Pat. No. 4,186,748 to Schlager describes a thermographic analytical apparatus for determining the presence of cancer and includes a pattern recognition program to provide an automated diagnosis of particular medical conditions.

None of this prior art, however, taken alone or in combination recognizes the problem that the computer-generated data, i.e., the computer's analysis of the sample prior to comparison with the data base, may be incorrect.

The preliminary work leading up to the present invention was published July 1981 in the Medical Laboratory Observer published by the Medical Economics Company of Oradell, N.J. 07649, entitled "Computerized Diagnosis in the Lab". The aforementioned article relates, in general, to the internal decision making process for programming a computer. The article explains that a scanning densitometer equipped with an interpretive program for serum protein electrophoresis is already undergoing testing and evaluation at the clinical laboratory of Overlook Hospital in Summit, N.J.

Of course, as the article correctly points out, once a working computer program model has been created, computer interpretations and computer diagnoses must be compared with the physician's independent diagnoses to confirm the accuracy of the computer model and, of course, the computer model must be repeatedly refined until the computer interpretation results in acceptable percentage of agreement with the physician's own diagnosis. At that point in time, according to standardized techniques, the computer program can be burned into a ROM and provided as a part of the densitometer.

To further understand the present invention, it should be understood that according to the aforementioned Golias et al patent, when a blood sample or the like which has been electrophoretically prepared is optically scanned, an analog signal is provided which is a function of the optical density of the scanned sample. The analog signal has a plurality of peaks and valleys and the integral of the analog signal, commonly referred to as the area under the curve, is representative of the total serum protein present in the sample. According to the prior art Golias et al patent, a microprocessor-controlled densitometer has the ability to select the valleys within the analog signal and separately compute the area under the curve between adjacent valleys thus providing the serum protein fractions referred to as albumin, alpha-1, alpha-2, beta and gamma. These individual fractions are quantified according to the prior art and the numerical values, percentages, and analog output are all utilized by the physician to assist in the diagnosis of the condition of the patient from whom the blood sample was obtained.

As previously indicated, the computer's determination of the location of the valleys (i.e., computer self-generated data) may not be correct. The physician has the analog curve available for use in diagnosis, which is critical if the physician disagrees with the computer's selection of the "valleys". But the prior art does not suggest the use of external data, including confirmation or modification of the computer-selected data (e.g., valleys).

Thus prior to the present invention the physician must accept the computer generated data in order to accept the "diagnosis" i.e., the comparison to the data base.

SUMMARY OF THE INVENTION

The present invention overcomes these shortcomings and solves the aforementioned problems by providing a system where the operator of the densitometer or the like must first accept or modify the computer's analysis of the sample and, thereafter, the computer will provide a preliminary medical diagnosis.

In the context of serum protein analysis, the present invention provides an improved diagnostic or data-interpretive densitometer system which requires densitometer operator intervention after a preliminary optical density analog output and selection of the valleys between the fractions has been made by the computer but prior to any analysis or comparison to a data base. The operator must accept or modify the selection of the valleys. The operator also provides additional data to the system. Thereafter, the densitometer provides a permanent record of the analog output, provides a permanent record of the amount of each of the serum protein fractions and generates an interpretive diagnosis of the data all dependent, in part, on the decision of the operator and the additional data from the operator.

The various other features and benefits of the present invention will become more apparent upon reading the following detailed description of the invention taken in conjunction with the drawings.

BRIEF DESCRIPTION OF THE DRAWINGS

In the drawings, wherein like reference numerals identifying corresponding components.

DETAILED DESCRIPTION OF THE PREFERRED EMBODIMENT OF THE PRESENT INVENTION

The present invention, which is an improvement of the single scan microprocessor-controlled densitometer described in Golias et al U.S. Pat. No. 4,242,730, the entire disclosure of which is hereby incorporated herein by reference, may be considered as having three basic aspects. The first aspect of the present invention is the scanning of the electrophoretically prepared blood sample to provide an analog output on an oscilloscope or cathode ray tube of the optical density of the sample and a preliminary selection of the valleys within the sample. The area under the curve between successive valleys are indicative of the various fractions within the blood sample, namely, albumin, alpha-1, alpha 2, beta and gamma. These fractions are, of course, well known in serum protein analysis.

The second aspect of the present invention requires intervention by the operator of the densitometer. The operator is to provide certain data about the patient, e.g., age, the operator must add, delete, modify or confirm the densitometer's automatic selection of the valleys so that there are exactly five fractions, and the operator should indicate various preliminary interpretations of the analog trace, all as will be explained in greater detail.

The third aspect of the present invention is the interpretive aspect where the densitometer evaluates the totality of data, namely, the analog trace as modified (or confirmed) by the operator and the operator's observations regarding the analog trace, computes the relative amounts of each of the fractions, compares the totality of data to the data base and automatically provides an output report including a most likely diagnosis.

Figure 1:
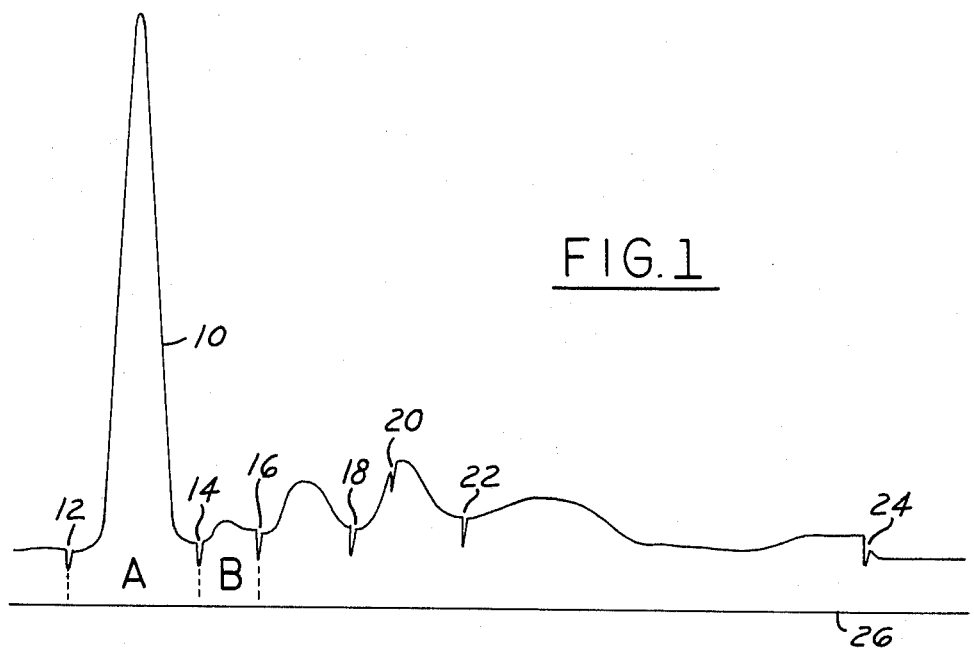
FIG. 1 is a graphic presentation of an analog output of the optical density of an electrophoretically prepared blood sample.

FIG. 1 illustrates a typical analog trace or output which is representative of the optical density scan of an electrophoretically prepared blood serum sample. This analog trace includes a plurality of valleys 12, 14, 16, 18, 20, 22 and 24 which are automatically generated in the microprocessor-controlled densitometer described in the aforementioned Golias et al patent. The analog trace 10 may be displayed on an oscilloscope or drawn on chart paper, relative to a base line or reference line 26. Between each pair of valleys the area under the curve and above the base line 26 would be indicative of the amount of each of the serum proteins. Since the densitometer detected seven valleys in the trace of FIG. 1, the densitometer would determine that there were six protein fractions. That is, a first fraction "A" between valleys 12 and 14, a second fraction "B" between valleys 14 and 16, etc. The densitometer determines the total area under the curve 10, the area under the curve for each fraction, and the percentage of each fraction to the total.

The interpretation of serum protein data, however, is based upon the presence of exactly five fractions. Thus one important aspect of the present invention which requires operator intervention is referred to as "verifying" the automatic selection of the valleys which was accomplished by the densitometer. As used herein, to verify the selection includes any combination of: confirming the number and location of one or more valleys, deleting one or more valleys, adding one or more valleys and moving one or more valleys. This may be explained by reference to FIG. 2 in comparison to FIG. 1.

Figure 2:
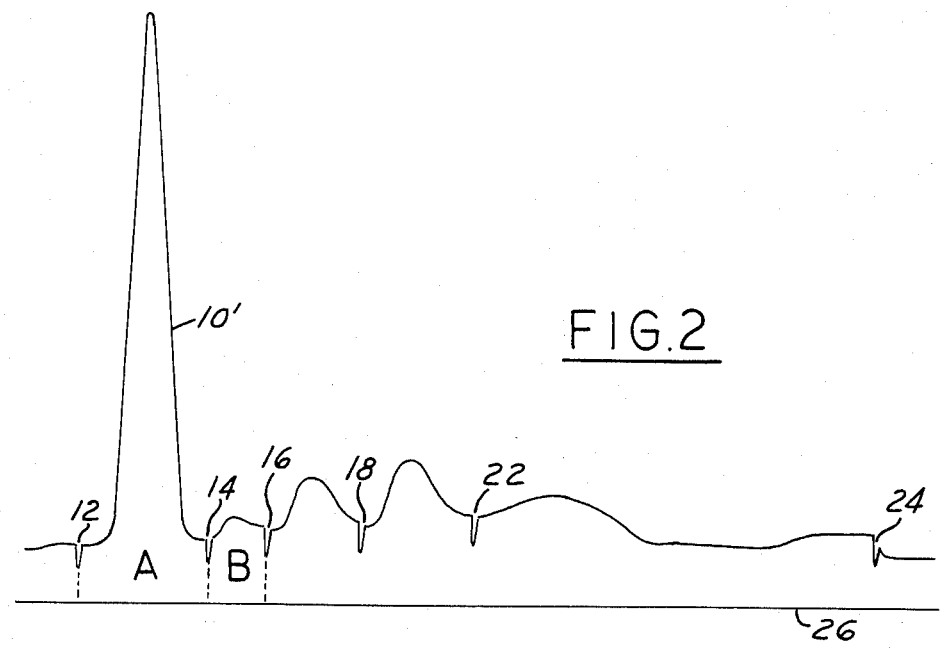
FIG. 2 is a representation of an analog output of FIG. 1 after it has been edited by the computer operator.

Assume that FIG. 1 is the oscilloscope trace generated by the densitometer, and that the densitometer operator determines that valley 20 was incorrect. FIG. 2 illustrates the oscilloscope trace of FIG. 1 which has been modified by the operator while the trace is displayed by moving a cursor to the computer selected valley 20 of FIG. 1 and deleting this valley. The resulting trace 10' of FIG. 2 has only six valleys (12, 14, 16, 18, 22 and 24) and thus only five fractions.

The operator intervention could also include moving densitometer-generated selection of any one or more of the valleys, adding valleys or confirming the acceptance by the operator of the computer selected valleys.

Hence the description of operator intervention with respect to FIG. 2, is provided merely as an illustration. With the foregoing as an illustration of operator intervention and verification, we turn now to the overall system of the present invention.

Figure 3:
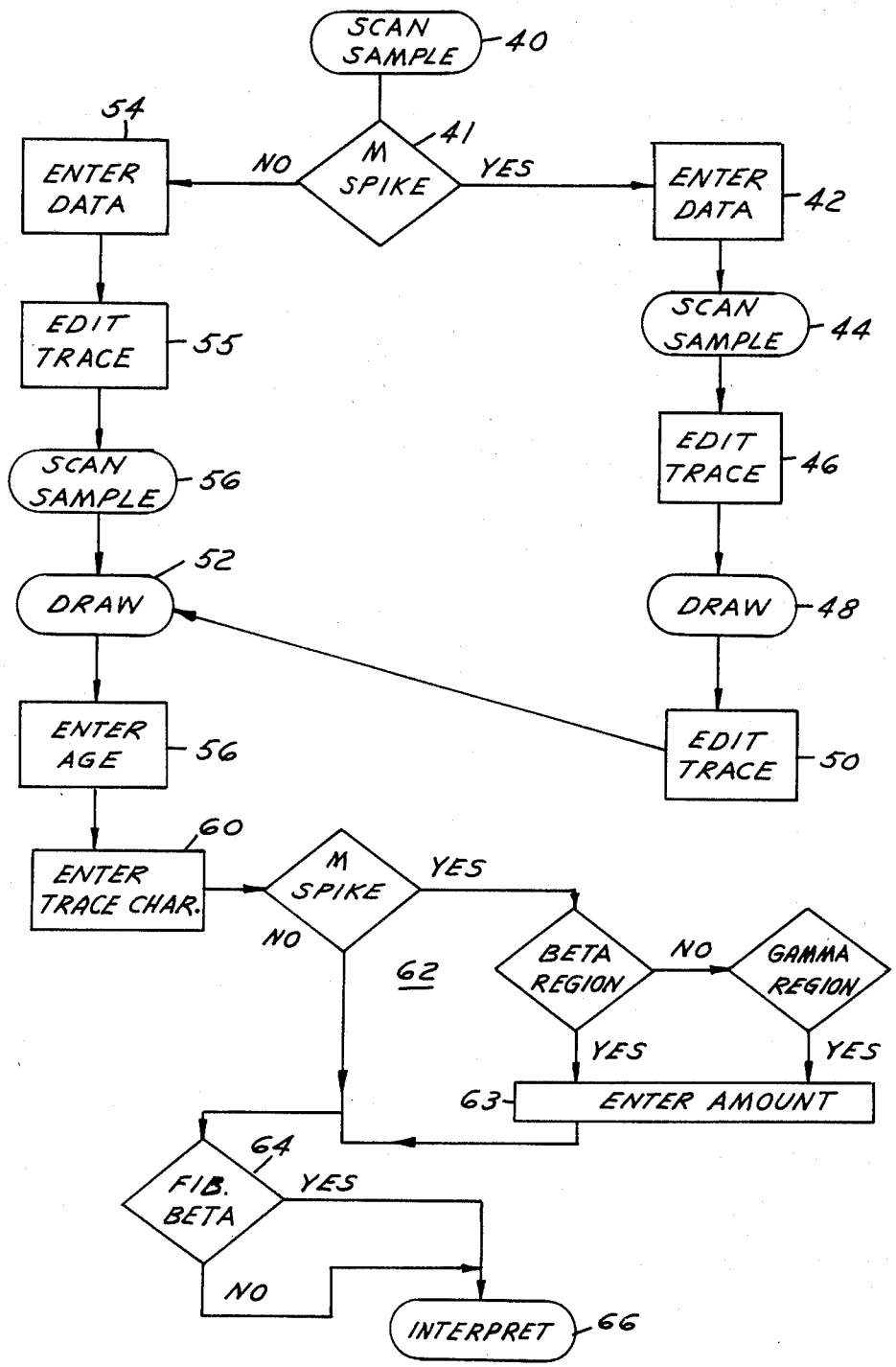
FIG. 3 is a flow chart of the computer logic for the interpretive program of the present invention.

Referring next to FIG. 3, a flow chart of the present system is illustrated. The flow chart and sequence of operations is explained as follows.

Initially, the electrophoretically separated blood sample is automatically scanned by the densitometer referred to in the aforementioned Golias U.S. Pat. No. 4,242,730 to provide on an oscilloscope of the densitometer a tracing of the optical density which illustrates the densitometer-selected locations of the valleys. The scanning of the patient sample and the presentation of the densitometer-generated analog signal and densitometer-generated locations of the valleys is the first step 40 in the flow chart.

Next, the system requires operator intervention and decision. As the operator observes the densitometer generated trace on the oscilloscope, the operator must decide, at 41 the presence or possible presence of a monoclonal or polyclonal spike (referred to as an M-spike). If the decision is YES, the operator at step 42 must enter data, specifically the total protein in the sample, via a conventional keyboard. The sample is again scanned, at step 44, to provide a new analog trace on the oscilloscope. The densitometer-generated trace, illustrated on the oscilloscope, will include a plurality of valleys and the operator of the densitometer must verify the presence and location of six fractions at step 46 on the flow chart. The next step 48 is drawing the pattern on the oscilloscope with the six fractions onto graph paper to make a first permanent record.

Next, the computer operator must again edit or verify as at 50 the densitometer-generated pattern on the oscilloscope to select only five fractions with the monoclonal spike or possible monoclonal spike included within either the beta or gamma fraction depending upon where it occurs. Thereafter, a second pattern is drawn 52 on the graph paper as a permanent record having only five fractions.

In the event that the first scan 40 of the patient sample does not indicate the presence of a spike or the presence of a possible spike, then the decision at step 41 would be NO. The operator would then enter data at step 54, specifically the total protein value via the keyboard. Next, at step 55, the operator edits or verifies the selection of five fractions (six valleys) by editing, adding, modifying, deleting or confirming the densitometer-generated tracing on the oscilloscope. The scan instruction 56 is given to again scan the sample and the "draw" instruction 52 is given so that the pattern is drawn on the graph paper. It should be pointed out that the interpretation of the sample insofar as the amount of each fraction, is based upon the edited scan which is drawn at step 52 containing exactly 5 fractions.

At this time, further operator intervention and data input is required. The operator must enter the age of the patient at step 58, because it is known, based upon the data base, that the normal gamma range varies as a function of age. The data base and interpretive data program requests the age of the patient in months if the patient is less than one year old and the age in years if the patient is at least one year old. The program assumes an age of 40 in any instance where the age of the patient is unknown.

The next step 60 requires the operator to examine the trace on the oscilloscope and select one of six characteristics. The characteristics are based upon the operator's experience and the six possible characteristics are (1) beta-gamma bridge; (2) M-spike present; (3) asymmetric gamma; (4) possible M-spike; (5) unusual pattern; or (6) none of the above. Characteristics 2 or 4 are selected if the decision at step 41 was YES. If the decision at step 41 was NO, one of the remaining characteristics is selected by the operator.

If the operator indicates a tracing characteristic 2 or 4 (an M-spike present or possible) the program enters a subroutine 62 in which the operator must identify whether the M-spike or possible M-spike is in the beta or gamma fraction and enters the intensity of the spike 63 (the area under the curve) in grams per deciliter.

The next step 64 requires the operator to evaluate the trace to determine whether a fibrinogin spike is present in the beta region and to indicate the presence or absence of such a spike at step 64. Thereafter, the operator, at step 66, instructs the densitometer to interpret the totality of data, namely, the densitometer-generated data, the operator verification and operator entered data and to compare the totality of data to the data base which has been provided to the system. The system will thereafter interpret the totality of data and provide a most likely diagnosis.

Figure 4:
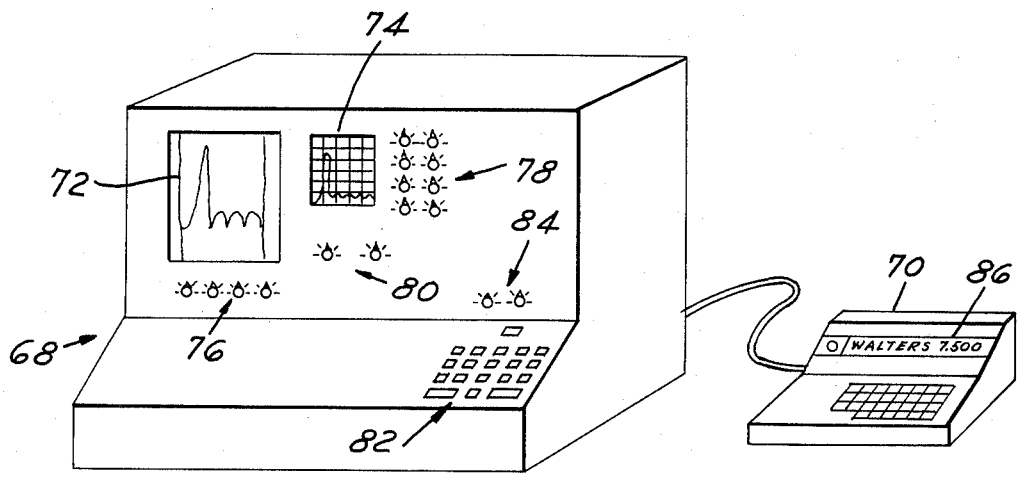
FIG. 4 is a perspective view of a diagnostic densitometer of the present invention.

Reference is now made to FIG. 4 which broadly depicts the diagnostic densitometer of the present invention. The densitometer includes a main console 68 and an ancillary keyboard 70. The console 68 includes a direct printer 72 for providing a hard copy of the electrophoraragram and a clinical interpretative analysis of the scanned pattern. A CRT oscilloscope 74 provides instantaneous graphical display of the serum protein pattern and is also used by the operator for manual editing of the electrophoresis pattern. A plurality of controls 78 allow positioning and editing the pattern as it is displayed on the CRT 74. Controls 80 permit selection of the filter wavelength for scanning and the size of the slit used to traverse the pattern. Controls 76 may be employed by the operator to select the length of the pattern as it is printed by the printer 72, the intensity of the print-out and maximum position of the printing element, as well as the position of the printing element relative to the hard copy chart paper. A pad 82 of control keys permit manual scanning, drawing and minor editing of the pattern by the operator.

The ancillary keyboard 70 includes a character line display 86 employing LEDs or the like. The keyboard 70 allows major editing of the pattern, and the display 86 presents the patient sequence number, patient name and total protein count. Controls 84 are provided to allow the operator to determine the zero or starting point of the printing element and the maximum gain deflection of the printing element employed in the printer 72.

Figure 5:
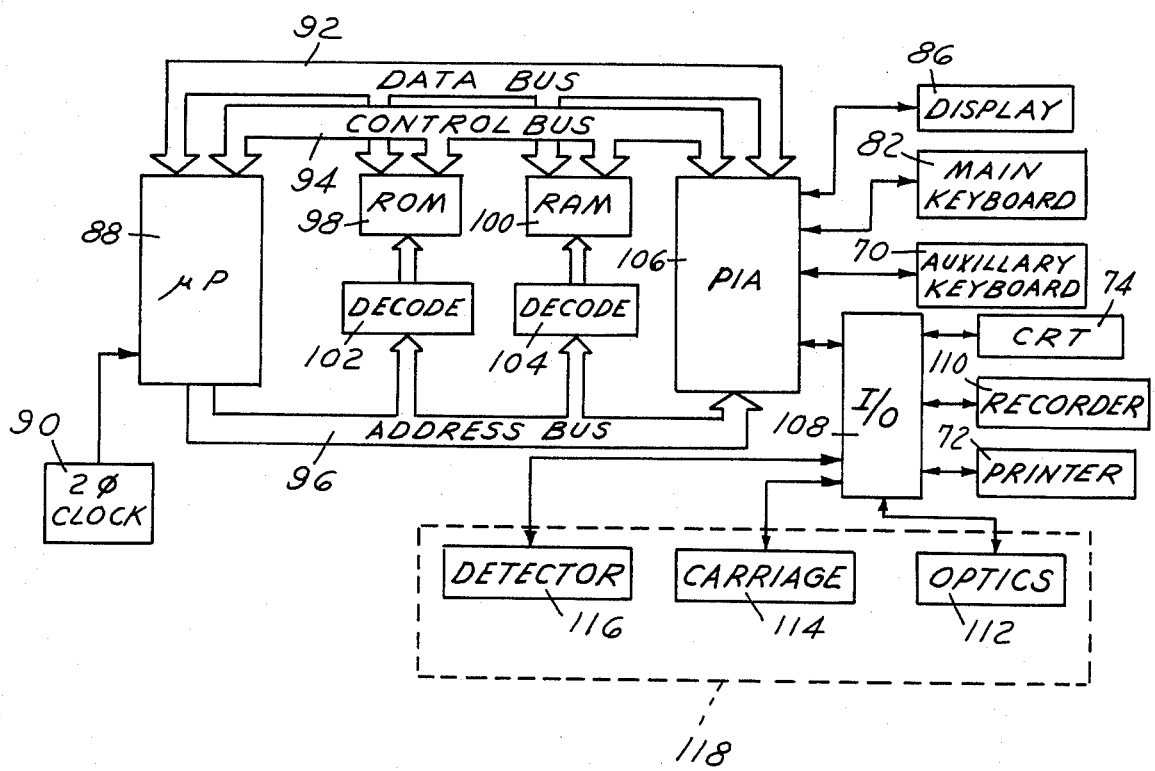
FIG. 5 is a block diagram of the circuit for the diagnostic densitometer of the present invention.

Attention is now directed to FIG. 5 which depicts, in block diagram form, one suitable circuit for use in the diagnostic densitometer of the present invention. The heart of the system is a microprocessor 88 that may comprise for example, a Motorola 6800 which is supplied with two phase clock pulses from a clock 90. The microprocessor 88 is interconnected to a ROM 98 (read-only memory), a RAM 100 (random access memory) and a peripheral interface adapter 106 (PIA). The microprocessor 88 communicates with ROM 98, RAM 100 and the PIA 106 by means of a data bus 92, control bus 94 and address bus 96. Address signals delivered by address bus 96 are decoded by decoders 102 and 104 and are employed to address memory locations in the ROM 98 and RAM 100. Typically, the address bus 96 will include 16 address lines and the data bus 92 will include eight data lines. The control bus 94 provides control signals which selectively enable ROM 98, RAM 100 and PIA 106. The PIA 106 provides digital outputs for the microprocessor 88 and is used to interface with external modules, such as an I/O (input/output) 108, the auxiliary keyboard 70, main keyboard 82 and display 86. The I/O 108 interconnects the microprocessor 88 with the printer 72, CRT 74 and a recorder 110. The I/O 108 also interconnects the microprocessor 88 with the circuitry 118 employed for scanning the serum samples. The circuitry 118 includes a scanning carriage 114 and associated control circuitry employed to move the serum sample to be analyzed with respect to optics 112 for optically sensing the serum sample. An optical detector 116 includes a photomultiplier tube for delivering electrical analog signals to the I/O 108.

The operating program for the system will typically be stored in the ROM 98, while the application program will normally be stored in the RAM 100 which forms an integral part of the system, or may be loaded into the system memory from an external source such as a disc or the like. The RAM 100 will also be employed to store the data base used in generating the interpretive diagnosis.

For the purpose of providing a complete description of the preferred embodiment, reference should be had to the listing of the computer program which is written in Basic. The program listing, which is hereby incorporated herein by reference, is a public document based upon an application for copyright registration thereof filed May 11, 1984 in the name of Helena Laboratories Corporation and identified as registration certificate No. TXu 160-457.

The foregoing, including the information incorporated by reference, is a complete description of the preferred embodiment of the present invention. Many changes and modifications can be made without departing from the spirit and scope of the present invention. The invention, therefore, should be limited only by the following claims.

What is claimed is:

1. A system for analyzing an electrophoretically separated blood serum sample comprising:
    densitometer means for optically scanning a blood serum sample and for providing at least a first visible output, said first visible output including a preliminary determination by the densitometer means of the blood serum protein fractions contained in said sample;
    microprocessor means connected to said densitometer means;
    said microprocessor means having a data base including at least the normal ranges of the blood serum protein fractions and diagnostic interpretations based upon deviations of one or more of said blood serum sample protein fractions from the normal ranges;
    said microprocessor means permitting manual external verification of the first visible output;
    said microprocessor means requiring the manual entry of external data for the sample being scanned, said external data being distinct from any data entered during manual external verification of the first visible output; and
    said microprocessor means generating a report based upon a comparison of the verified visible output and the manually entered external data with data in the data base.

2. The system as defined in claim 1 wherein said report includes a diagnostic interpretation which indicates the most likely medical condition evidenced by the scanned sample and manually entered external data.

3. The system as defined in claim 2 wherein said report also includes an analog representation of the verified visible output.

4. The system as defined in claim 3 wherein said report also includes a digital representation of the amount of each blood serum protein fraction in the blood serum sample.

5. The system as defined in claim 1 wherein the manual external data includes the age of the patient from whom the sample was taken.

6. The system as defined in claim 1 wherein the manual external data includes a determination of the characteristics of the first visible output.

7. The system as defined in claim 1 wherein the external data to be entered is data based upon a manual interpretation of the first visible output.

8. The system as defined in claim 7 wherein the first visible output is a trace, and said blood serum protein fractions include fractions at least for albumin, alpha 1 globulin, alpha-2 globulin, beta-globulin and gamma-globulin.

9. The system as defined in claim 8 wherein the external data to be entered represents at least one characteristic of the trace selected from the group of possible characteristics consisting of (1) beta-gamma bridge, (2) M-spike present, (3) asymmetric gamma, (4) possible M-spike, (5) unusual pattern, and (6) none of the characteristics (1) through (5).

10. The system as defined in claim 8 wherein the external data to be entered represents whether an M-spike or possible M-spike which is present in the trace is present in the region of the beta-globulin fraction or in the region of the gamma-globulin fraction.

11. The system as defined in claim 8 wherein the external data to be entered represents whether a fibrinogen spike is present in the trace.

12. A method of operating a densitometer for analysis of blood serum proteins or the like with the aid of a computer, comprising:
    providing said computer with a data base including at least the normal ranges of blood serum protein fractions and possible interpretations depending upon the amount of each of said blood serum protein fractions in a scanned sample;
    providing said densitometer with a blood serum sample;
    optically scanning said blood serum sample and providing at least a first visible output trace which is an analog function of the optical density of the scanned sample;
    said step of optically scanning said sample and providing said first visible output trace including indicating on said first visible output trace a plurality of valleys;
    verifying said first visible output trace so that exactly six valleys are indicated on said first visible output trace;

optically scanning said blood serum sample and determining the area under the verified first visible output trace and between each pair of adjacent valleys, said area indicative of each of the five blood serum protein fractions in the sample;

manually providing to the computer external data for the sample being scanned, said external data being distinct from any data provided during the step of verifying said first visible output trace; and comparing, in said computer, said manually provided external data, said verified first visible output trace and said fractions with data in said data base and generating a written diagnostic interpretation of the most likely medical analysis of the optically scanned sample in conjunction with said verifying thereof and said manually provided external data.

13. The method as defined in claim 12 wherein said step of optically scanning said sample is also followed by a step of manually evaluating said first visible output trace and said step of manually providing external data to the computer includes providing data based upon said manual evaluation of said first visible output trace.

14. The method as defined in claim 13 wherein said manual evaluation of said first visible output includes a determination of whether an M-spike is present in said trace, and said step of manually providing external data includes providing external data indicating whether said M-spike is present.

15. In a method of scanning an electrophoretically prepared blood sample in a densitometer and providing at least a first visible output trace which is an analog representation of the optical density of the scanned blood sample including indicating on said first visible output trace a plurality of valleys, the improvement comprising:

providing a digital computer with a data base;

verifying said first visible output trace so that exactly six valleys are indicated; manually providing to said computer external data indicating the presence or absence of an M-spike, said external data being distinct from any data entered during the verifying step; and comparing in said digital computer said verified first visible output trace and said external data with data in said data base to provide a medical diagnosis.

16. The improvement as defined in claim 15 wherein said step of verifying includes adding at least one valley.

17. The improvement as defined in claim 15 wherein said step of verifying includes deleting at least one valley.

18. The improvement as defined in claim 15 wherein said step of verifying includes confirming the densitometer-selected valleys.

19. The improvement as defined in claim 15 and further including manually providing said densitometer with additional external data from a preliminary interpretation of the characteristics of said first visible output trace.

20. The system as defined in claim 19 wherein said first visible output trace also includes peaks between said valleys representative of the quantities of five proteins, namely albumin, alpha-1 globulin, alpha-2 globulin, beta-globulin and gamma-globulin, which are present in said blood sample, and said additional external data to be entered represents at least one characteristic of the trace selected from the group of possible characteristics consisting of: (1) beta-gamma bridge, (2) an M-spike present or possibly present, (3) asymmetric gamma, and (4) fibrinogen spike.

* * * * *